(12) United States Patent
Eddy et al.

(10) Patent No.: US 11,207,532 B2
(45) Date of Patent: Dec. 28, 2021

(54) DYNAMIC SENSING UPDATES USING POSTURAL INPUT IN A MULTIPLE DEVICE CARDIAC RHYTHM MANAGEMENT SYSTEM

(71) Applicant: CARDIAC PACEMAKERS, INC., St. Paul, MN (US)

(72) Inventors: Steven Lee Eddy, Chesterfield, VA (US); Brendan Early Koop, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 765 days.

(21) Appl. No.: 15/857,298

(22) Filed: Dec. 28, 2017

(65) Prior Publication Data

US 2018/0185660 A1 Jul. 5, 2018

Related U.S. Application Data

(60) Provisional application No. 62/442,234, filed on Jan. 4, 2017.

(51) Int. Cl.
*A61N 1/372* (2006.01)
*A61N 1/375* (2006.01)
(Continued)

(52) U.S. Cl.
CPC ........ *A61N 1/37288* (2013.01); *A61B 5/0024* (2013.01); *A61B 5/0031* (2013.01);
(Continued)

(58) Field of Classification Search
CPC ............ A61N 1/37288; A61N 1/39622; A61N 1/37512; A61N 1/36535; A61N 1/36542
See application file for complete search history.

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Joseph M Dietrich
(74) *Attorney, Agent, or Firm* — Seager, Tufte & Wickhem LLP

(57) ABSTRACT

Methods and systems in which a first medical device provides patient status details to a second medical device. Patient status details may include one or more of patient posture and/or patient activity level, or other indications of patient status. The second medical device, in response to information about patient status and changes in patient status, uses a sensing configuration management function to respond to and accommodate the change in patient status. In an example, a first medical device monitors patient posture and communicates information related to patient posture to a second medical device, which then tailors sensing configurations to the patient posture.

20 Claims, 6 Drawing Sheets

(51) Int. Cl.

| | | |
|---|---|---|
| *A61N 1/39* | (2006.01) | |
| *A61N 1/37* | (2006.01) | |
| *A61B 5/11* | (2006.01) | |
| *A61B 5/00* | (2006.01) | |
| *A61B 5/35* | (2021.01) | |
| *A61B 5/287* | (2021.01) | |
| *A61B 5/341* | (2021.01) | |
| *A61B 5/352* | (2021.01) | |
| *A61B 5/361* | (2021.01) | |
| *A61B 5/363* | (2021.01) | |

(52) U.S. Cl.
CPC .......... *A61B 5/1116* (2013.01); *A61B 5/1118* (2013.01); *A61B 5/287* (2021.01); *A61B 5/341* (2021.01); *A61B 5/35* (2021.01); *A61B 5/352* (2021.01); *A61B 5/361* (2021.01); *A61B 5/363* (2021.01); *A61B 5/686* (2013.01); *A61B 5/6869* (2013.01); *A61N 1/3704* (2013.01); *A61N 1/3756* (2013.01); *A61N 1/37512* (2017.08); *A61N 1/3925* (2013.01); *A61N 1/39622* (2017.08); *A61B 2560/0468* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |

(56) References Cited

U.S. PATENT DOCUMENTS

| | | |
|---|---|---|
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |

(56) References Cited

U.S. PATENT DOCUMENTS

| | | |
|---|---|---|
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisker et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |

(56) References Cited

U.S. PATENT DOCUMENTS

| | | |
|---|---|---|
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |

(56) References Cited

U.S. PATENT DOCUMENTS

| | | |
|---|---|---|
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |

(56) References Cited

U.S. PATENT DOCUMENTS

| | | |
|---|---|---|
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |

(56) References Cited

U.S. PATENT DOCUMENTS

| | | |
|---|---|---|
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |

(56) References Cited

U.S. PATENT DOCUMENTS

| | | |
|---|---|---|
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |

(56) References Cited

U.S. PATENT DOCUMENTS

| | | |
|---|---|---|
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Seyedi et al., "A Survey on Intrabody Communications for Body Area Network Application," IEEE Transactions on Biomedical Engineering, vol. 60(8): 2067-2079, 2013.

DYNAMIC SENSING UPDATES USING POSTURAL INPUT IN A MULTIPLE DEVICE CARDIAC RHYTHM MANAGEMENT SYSTEM

CROSS REFERENCE TO RELATED APPLICATIONS

The present application claims the benefit of and priority to U.S. Provisional Patent Application Ser. No. 62/442,234, filed on Jan. 4, 2017, and titled DYNAMIC SENSING UPDATES USING POSTURAL INPUT IN A MULTIPLE DEVICE CARDIAC RHYTHM MANAGEMENT SYSTEM, the disclosure of which is incorporated herein by reference.

BACKGROUND

The Subcutaneous Implantable Cardioverter-Defibrillator (such as the Emblem S-ICD System™, Boston Scientific Corp.), uses sensing electrodes disposed subcutaneously, outside the ribcage of the patient, to discern whether a treatable arrhythmia is occurring and makes therapy decisions accordingly. Characteristics of the sensed signal from such electrodes can vary depending on patient posture, activity, and/or other characteristics of the patient's present state. New and alternative methods and systems that allow such a system to identify postural changes and dynamically address such changes in a sensing algorithm are desired.

Overview

The present inventors have recognized, among other things, that a problem to be solved is the desire to dynamically optimize sensing of a cardiac rhythm management system as patient status changes. Patient status may include, for example, changes in activity level or posture of the patient.

A first illustrative, non-limiting example takes the form of a system for treating a patient comprising: a first medical device comprising a status sensor for at least sensing changes in patient status, and a first communication circuit for generating a communication output; a second medical device in the form of an implantable medical device comprising a plurality of electrodes for receiving cardiac electrical signals, operational circuitry operable to sense cardiac rhythms of the patient using at least the received cardiac electrical signals, and a second communication circuit; wherein the first communication circuit is configured to communicate to the second communication circuit, and the second communication circuit is configured to at least receive communication from the first communication circuit; further wherein: the first medical device comprises a patient status sensor configured to sense whether a patient status is changing or has changed, and the first medical device is configured to use the first communication circuit to communicate to the second communication circuit in response to sensing that the patient status is changing or has changed; and the second medical device operational circuitry is configured to analyze or adjust a sensing configuration used by the second medical device to sense cardiac rhythms of the patient in response to the second communication circuit receiving a communication from the first communication circuit.

Additionally or alternatively to the first illustrative, non-limiting example and variants thereof, the status sensor may include a posture sensor for at least sensing changes in patient posture; the first medical device may be configured to use the first communication circuit to communicate to the second communication circuit in response to the posture sensor sensing that the patient posture is changing or has changed to indicate a change in posture status of the patient; and the second medical device may be configured to analyze a sensing vector configuration used for ventricular activity sensing in response to the first medical device communicating a change in posture status of the patient.

Additionally or alternatively to the first illustrative, non-limiting example and variants thereof, the status sensor may include a posture sensor for at least sensing changes in patient posture; the first medical device may be configured to use the first communication circuit to communicate to the second communication circuit in response to the posture sensor sensing that the patient posture is changing or has changed to indicate a change in posture status of the patient; and the second medical device may be configured to analyze a sensing vector configuration used for atrial activity sensing in response to the first medical device communicating a change in posture status of the patient.

Additionally or alternatively to the first illustrative, non-limiting example and variants thereof, the status sensor may include an activity sensor for at least sensing changes in patient activity level; and the first medical device may be configured to use the first communication circuit to communicate to the second communication circuit in response to the activity sensor sensing that the patient activity level is changing or has changed to communicate a change in activity status of the patient; the second medical device may be configured to analyze a sensing vector configuration used for ventricular activity sensing in response to the first medical device communicating a change in activity status of the patient.

Additionally or alternatively to the first illustrative, non-limiting example and variants thereof, the status sensor may include an activity sensor for at least sensing changes in patient activity level; and the first medical device may be configured to use the first communication circuit to communicate to the second communication circuit in response to the activity sensor sensing that the patient activity level is changing or has changed to communicate a change in activity status of the patient; the second medical device may be configured to analyze a sensing vector configuration used for atrial activity sensing in response to the first medical device communicating a change in activity status of the patient.

Additionally or alternatively to the first illustrative, non-limiting example and variants thereof, the status sensor may include a posture sensor for at least sensing changes in patient posture; the first medical device may be configured to use the first communication circuit to communicate to the second communication circuit in response to the posture sensor sensing that the patient posture is changing or has changed to indicate a change in posture status of the patient; and the second medical device may be configured to modify, reform, or switch a template used in analyzing ventricular activity sensing in response to the first medical device communicating a change in posture status of the patient.

Additionally or alternatively to the first illustrative, non-limiting example and variants thereof, the status sensor may include a posture sensor for at least sensing changes in patient posture; the first medical device may be configured to use the first communication circuit to communicate to the second communication circuit in response to the posture sensor sensing that the patient posture is changing or has changed to indicate a change in posture status of the patient;

and the second medical device may be configured to modify, reform, or switch a template used in analyzing atrial activity sensing in response to the first medical device communicating a change in posture status of the patient.

Additionally or alternatively to the first illustrative, non-limiting example and variants thereof, the status sensor may include an activity sensor for at least sensing changes in patient activity level; and the first medical device may be configured to use the first communication circuit to communicate to the second communication circuit in response to the activity sensor sensing that the patient activity level is changing or has changed to communicate a change in activity status of the patient; the second medical device may be configured to modify, reform, or switch a template used in analyzing ventricular activity sensing in response to the first medical device communicating a change in activity status of the patient.

Additionally or alternatively to the first illustrative, non-limiting example and variants thereof, the status sensor may include an activity sensor for at least sensing changes in patient activity level; and the first medical device may be configured to use the first communication circuit to communicate to the second communication circuit in response to the activity sensor sensing that the patient activity level is changing or has changed to communicate a change in activity status of the patient; the second medical device may be configured to modify, reform, or switch a template used in analyzing atrial activity sensing in response to the first medical device communicating a change in activity status of the patient.

Additionally or alternatively to the first illustrative, non-limiting example and variants thereof, the system may further comprise a third medical device comprising a status sensor for sensing at least one of a patient status or changes in patient status, and third communication circuit configured for communication to at least the second communication circuit; wherein the operational circuitry of the second medical device may be configured to observe data received from each of the first and third medical devices as to the patient status and determine, or augment a determination of, the patient's cardiac rhythm. Additionally or alternatively, each of the first and third medical devices may be a leadless cardiac pacemaker for implantation on or adjacent the heart; the second medical device may be an implantable defibrillator; the status sensors of the first and third medical devices may comprise motion sensors; and the second medical device may be configured to differentiate at least one of atrial fibrillation, ventricular tachycardia, and ventricular fibrillation, from sinus rhythm using the data received from each of the first and third medical devices as to the patient status.

Additionally or alternatively to the first illustrative, non-limiting example and variants thereof, the operational circuitry of the second medical device may be configured for sensing P-waves and R-waves of the patient's heart in separate data streams with: a P-wave detection sensing vector and P-wave template used in a data stream for the P-waves; and an R-wave detection sensing vector and R-wave template used in a data stream for the R-waves; and further wherein the operational circuitry may be configured to analyze and/or change at least two of these settings in response to receiving a communication generated by the first medical device in response to a sensed change in patient status: the P-wave detection sensing vector; the P-wave template; the R-wave detection sensing vector; and the R-wave template.

Additionally or alternatively to the first illustrative, non-limiting example and variants thereof, the first medical device may be a leadless cardiac pacemaker configured for implantation in or on the heart of a patient, and the second medical device may be an implantable defibrillator.

A second illustrative, non-limiting example takes the form of an implantable medical device (IMD) comprising a housing containing operational circuitry, the housing adapted to couple to a lead having one or more electrodes thereon to allow the operational circuitry to use the one or more electrodes to sense cardiac rhythms of a patient, the operational circuitry including a communication circuit for communicating with a second medical device, wherein the operational circuitry may be configured to: receive a communication using the communication circuit from the second medical device, the communication indicating a change in a patient status; and in response to receiving the communication indicating a change in patient status, analyze or adjust a sensing configuration used by the operational circuitry to sense cardiac rhythms of the patient.

Additionally or alternatively to the second illustrative, non-limiting example and variants thereof, the communicated patient status may be a patient posture; and the IMD may be configured to analyze a sensing vector configuration used for ventricular activity sensing in response to the second medical device communicating a change in patient posture.

Additionally or alternatively to the second illustrative, non-limiting example and variants thereof, the communicated patient status may be a patient posture; and the IMD may be configured to analyze a sensing vector configuration used for atrial activity sensing in response to the second medical device communicating a change in patient posture.

Additionally or alternatively to the second illustrative, non-limiting example and variants thereof, the communicated patient status may be a patient activity level; and the IMD may be configured to analyze a sensing vector configuration used for ventricular activity sensing in response to the second medical device communicating a change in patient activity level.

Additionally or alternatively to the second illustrative, non-limiting example and variants thereof, the communicated patient status may be a patient activity level; and the IMD may be configured to analyze a sensing vector configuration used for atrial activity sensing in response to the second medical device communicating a change in patient activity level.

Additionally or alternatively to the second illustrative, non-limiting example and variants thereof, the communicated patient status may be a patient posture; and the IMD may be configured to modify, reform, or switch a template used for ventricular activity sensing in response to the second medical device communicating a change in patient posture.

Additionally or alternatively to the second illustrative, non-limiting example and variants thereof, the communicated patient status may be a patient posture; and the IMD may be configured to modify, reform, or switch a template used for atrial activity sensing in response to the second medical device communicating a change in patient posture.

Additionally or alternatively to the second illustrative, non-limiting example and variants thereof, the communicated patient status may be a patient activity level; and the IMD may be configured to modify, reform, or switch a template used for ventricular activity sensing in response to the second medical device communicating a change in activity level of the patient.

Additionally or alternatively to the second illustrative, non-limiting example and variants thereof, the communication circuitry may be configured to communicate with a third medical device and receive patient status information therefrom; wherein the operational circuitry of the IMD may be configured to observe data received from each of the second and third medical devices as to the patient status and determine, or augment a determination of, the patient's cardiac rhythm. Additionally or alternatively, the operational circuitry may be configured to receive patient status information from the second and third medical devices comprising motion information generated by motion sensors of the second and third medical devices; and the IMD may be configured to differentiate at least one of atrial fibrillation, ventricular tachycardia, and ventricular fibrillation, from sinus rhythm using the motion data received from each of the second and third devices.

Additionally or alternatively to the second illustrative, non-limiting example and variants thereof, the operational circuitry of the IMD may be configured for sensing P-waves and R-waves of the patient's heart in separate data streams with: a P-wave detection sensing vector and P-wave template used in a data stream for the P-waves; and an R-wave detection sensing vector and R-wave template used in a data stream for the R-waves; and in response to receiving a communication indicating a change in patient status from the second medical device, the operational circuitry of the IMD may be configured to analyze and/or change at least two of these settings: the P-wave detection sensing vector; the P-wave template; the R-wave detection sensing vector; and the R-wave template.

A third illustrative, non-limiting example takes the form of a method of operation of a system as in the first illustrative, non-limiting example and variants thereof, or an IMD as in the second illustrative non-limiting example to monitor cardiac rhythms of a patient.

A fourth illustrative, non-limiting example takes the form of a method of operation in an implantable medical device system, the system comprising: a first medical device comprising a status sensor for at least sensing changes in patient status, and a first communication circuit for generating a communication output; a second medical device in the form of an implantable medical device comprising a plurality of electrodes for receiving cardiac electrical signals, operational circuitry operable to sense cardiac rhythms of the patient using at least the received cardiac electrical signals, and a second communication circuit; the method comprising: the first medical device sensing a change in patient status; the first medical device communicating to the second medical device to indicate sensing of a change in patient status; the second medical device receiving the communication from the first medical device indicating sensing of a change in patient status and, in response thereto, the second medical device analyzing or adjusting a sensing configuration used by the second medical device to sense cardiac rhythms of the patient.

Additionally or alternatively to the fourth illustrative, non-limiting example and variants thereof, the patient status sensed by the first medical device may be a patient posture, and the sensing configuration that is analyzed or adjusted may be a sensing vector configuration used for ventricular activity sensing.

Additionally or alternatively to the fourth illustrative, non-limiting example and variants thereof, the patient status sensed by the first medical device may be a patient posture, and the sensing configuration that is analyzed or adjusted may be a sensing vector configuration used for atrial activity sensing.

Additionally or alternatively to the fourth illustrative, non-limiting example and variants thereof, the patient status sensed by the first medical device may be a patient activity level, and the sensing configuration that is analyzed or adjusted may be a sensing vector configuration used for ventricular activity sensing.

Additionally or alternatively to the fourth illustrative, non-limiting example and variants thereof, the patient status sensed by the first medical device may be a patient activity level, and the sensing configuration that is analyzed or adjusted may be a sensing vector configuration used for atrial activity sensing.

Additionally or alternatively to the fourth illustrative, non-limiting example and variants thereof, the patient status sensed by the first medical device may be a patient posture, the sensing configuration that is analyzed or adjusted may be a template used for ventricular activity sensing, and the template may be analyzed or adjusted by at least one of switching, modifying, or reforming the template.

Additionally or alternatively to the fourth illustrative, non-limiting example and variants thereof, the patient status sensed by the first medical device may be a patient posture, the sensing configuration that is analyzed or adjusted may be a template used for atrial activity sensing, and the template may be analyzed or adjusted by at least one of switching, modifying, or reforming the template.

Additionally or alternatively to the fourth illustrative, non-limiting example and variants thereof, the patient status sensed by the first medical device may be a patient activity level, the sensing configuration that is analyzed or adjusted may be a template used for ventricular activity sensing, and the template may be analyzed or adjusted by at least one of switching, modifying, or reforming the template.

Additionally or alternatively to the fourth illustrative, non-limiting example and variants thereof, the patient status sensed by the first medical device may be a patient activity level, the sensing configuration that is analyzed or adjusted may be a template used for atrial activity sensing, and the template may be analyzed or adjusted by at least one of switching, modifying, or reforming the template.

Additionally or alternatively to the fourth illustrative, non-limiting example and variants thereof, wherein the system further comprises a third medical device comprising a status sensor for sensing at least one of a patient status or changes in patient status, and third communication circuit configured for communication to at least the second communication circuit; wherein the method further comprises the operational circuitry of the second medical device receiving from each of the first and third medical devices patient status data and determining, or augmenting a determination of, the patient's cardiac rhythm. Additionally or alternatively, each of the first and third medical devices may be a leadless cardiac pacemaker for implantation on or adjacent the heart; the second medical device may be an implantable defibrillator; the status sensors of the first and third medical devices comprise motion sensors; and the step of the second medical device determining or augmenting a determination of the patients cardiac rhythm comprises the second medical device differentiating at least one of atrial fibrillation, ventricular tachycardia, and ventricular fibrillation, from sinus rhythm using motion data received from each of the first and third medical devices. Additionally or alternatively, the first medical device may be placed to capture atrial motion, and the third medical device may be placed to capture ventricular motion.

Additionally or alternatively to the fourth illustrative, non-limiting example and variants thereof, the operational circuitry of the second implantable medical device may be configured for sensing P-waves and R-waves of the patient's heart in separate data streams with: a P-wave detection sensing vector and P-wave template used in a data stream for the P-waves; and an R-wave detection sensing vector and R-wave template used in a data stream for the R-waves; and the step of the second medical device analyzing or adjusting a sensing configuration used by the second medical device to sense cardiac rhythms of the patient comprises changing at least two of these settings: the P-wave detection sensing vector; the P-wave template; the R-wave detection sensing vector; and the R-wave template.

Additionally or alternatively to the fourth illustrative, non-limiting example and variants thereof, the first implantable medical device may be a leadless cardiac pacemaker configured for implantation in or on the heart of a patient and configured to provide pacing therapy to the heart of the patient, and the second implantable medical device may be an implantable defibrillator configured to provide defibrillation therapy to the heart of the patient.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
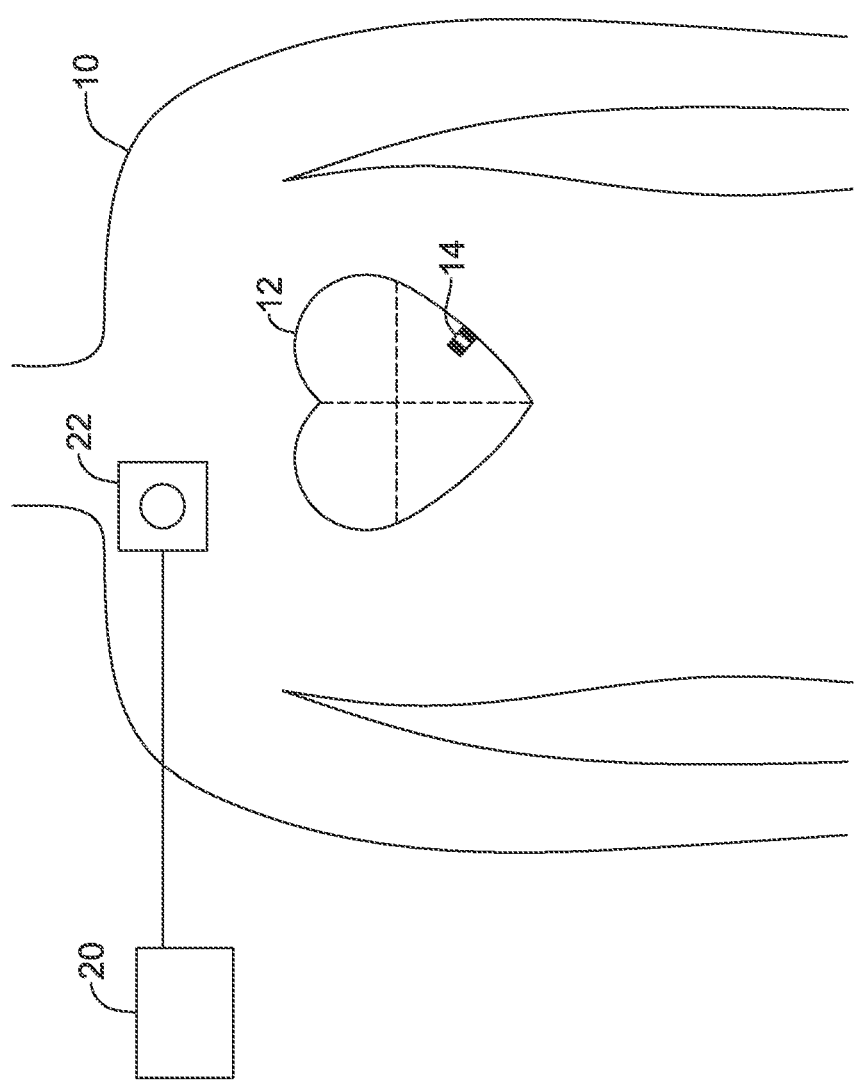
FIG. 1 illustrates a patient having an implantable leadless cardiac pacemaker (LCP) implanted in the left ventricle.

FIG. 1 illustrates a patient 10 having an implanted leadless cardiac pacemaker (LCP) 14 placed in the left ventricle of the patient's heart 12. The LCP 14 may be implanted at other locations, such as in the right ventricle, the right atrium, the right atrial appendage, the left atrium, the left atrial appendage, the coronary sinus, and/or epicardial cardiac veins or other blood vessels or locations in, on, or near the heart. A plurality of LCP devices may be implanted such as by having one or more atrial devices and one or more ventricular devices, or by having two ventricular devices, for example.

The LCP 14 is configured for communication with an external device 20 which may be, for example, a clinician programmer or, in some embodiments, may be some other device such as a mobile phone usable by the patient or a remote monitoring apparatus. The external device 20 may perform various processes and methods known in the art such as setting therapy or sensing parameters of the LCP and/or obtaining device diagnostics/settings as well as patient history or other information from the LCP 14.

Communication between the LCP 14 and external device 20 may use an optional wand 22 that can be placed on or near the patient to facilitate communication. For example the wand may be designed with two or more skin contact electrodes for conducted communication with an implantable device. Alternatively the wand may comprise a coil or antenna to facilitate inductive or radiofrequency communications, or may include an optical element(s) for infrared communication, or a transmitter and receiver for ultrasound communications, as desired. For example, Medradio communications in the 401-406 MHz band, Bluetooth or Bluetooth Low Energy, or Zigbee or other communications mode, may be facilitated by the provision of appropriate antennae and associated circuitry. The wand may be omitted and the antenna and associated circuitry may be provided within or on the external device 20. Though not shown in detail, the external device 20 may include any suitable user interface, including a screen, buttons, keyboard, touchscreen, speakers, and various other features widely known in the art.

The LCP 14 may include at least two therapy delivery electrodes to act as anode and cathode for therapy delivery. The LCP 14 may be placed by advancing a catheter into the heart from, for example, a femoral location, and attaining access to the left ventricle and placing the LCP 14 adjacent to the myocardium and engaging attachment features, such as tines, hooks, or helical coils, for example, thereto. Delivery, tissue attachment and retrieval features may be included in the LCP including those features shown in US PG Pat. Pub. No. 20150051610, titled LEADLESS CARDIAC PACEMAKER AND RETRIEVAL DEVICE, and US PG Pat. Pub. No. 20150025612, titled SYSTEM AND METHODS FOR CHRONIC FIXATION OF MEDICAL DEVICES, the disclosures of which are incorporated herein by reference. Delivery, fixation and retrieval structures may also resemble that of the Micra™ (Medtronic) or Nanostim™ (St. Jude Medical) leadless pacemakers.

The LV placement may be particularly useful for cardiac resynchronization therapy (CRT) purposes. Some patients may also or instead need a right ventricle (RV) located LCP to facilitate CRT, or to provide bradycardia or other therapy. Other patients may need an LCP in an atrial position to address an atrial dysfunction. Some patients may have multiple LCP devices implanted to address, for example, heart block(s) and/or CRT needs.

Figure 2:
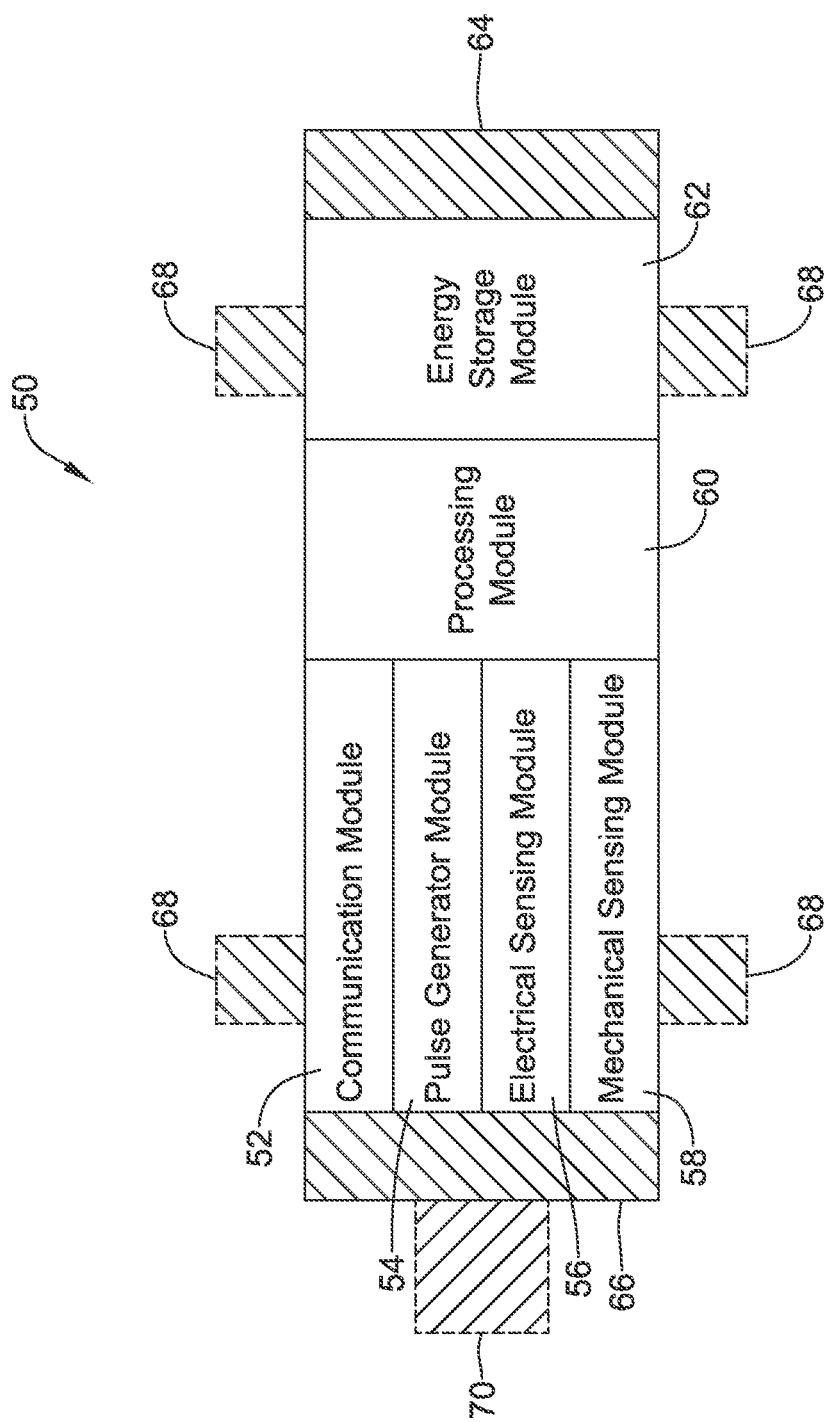
FIG. 2 shows an illustrative implantable leadless cardiac pacemaker.

FIG. 2 shows an illustrative LCP design. The LCP 50 is shown as including several functional blocks including a communications module 52, a pulse generator module 54, an electrical sensing module 56, and a mechanical sensing module 58. In some examples, the electrical sensing module 56 and mechanical sensing module 58 may be configured to sense one or more biological signals for use in one or more of determining timing for therapy, identifying physiological conditions related to the status of the patient.

In some examples, the mechanical sensing module 58 may include a motion sensor that can be used to identify patient activity. In some examples, the mechanical sensing module 58 may include a posture sensor that can be used to identify patient posture and/or changes in patient posture. For example, a motion or posture sensor may include a one or more of single-axis or multi-axis accelerometers. Some illustrative mechanical sensing modules and uses thereof are disclosed in US PG Pat. Pub. No. 20170056665, titled TEMPORAL CONFIGURATION OF A MOTION SENSOR IN AN IMPLANTABLE MEDICAL DEVICE, and/or US PG Pat. Pub. No. 20170056666, titled SPATIAL CONFIGURATION OF A MOTION SENSOR IN AN IMPLANTABLE MEDICAL DEVICE, the disclosure of which are incorporated herein by reference.

Motion may be detected by identifying, within a set of parameters, movement as detected using the accelerometer (s) such as by selective frequency filtering and/or temporal or other selection to avoid sensing non-movement noise (since the LCP is in and/or attached to the heart, filtering cardiac motion may be a goal). Posture may be detected using similar inputs, but with different components of the signal chosen by, for example, the use of different frequency filtering and/or the use of longer term trending of data outputs to observe a change from a first point in time to a second point in time. In an example, posture changes may be observed by looking for static offset in one or more posture sense vectors and/or a combination of such vectors, while gross body movement and the beating heart would be observable using more dynamic, frequency based changes.

A processing module 60 may receive data from and generate commands for outputs by the other modules 52, 54, 56, 58. An energy storage module is highlighted at 62 and may take the form of a rechargeable or non-rechargeable battery, or a supercapacitor, or any other suitable element.

Various details and/or examples of internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 64 and a second end electrode at 66. A retrieval feature is shown schematically at 70 and may be, for example, a short post with an opening therethrough to receive a retrieval hook. A number of tines 68 may extend from the device in several directions. The tines 68 may be used to secure the device in place within a heart chamber. An attachment structure may instead take the form of a helical screw, if desired. In some examples, tines 68 are used as the only attachment features. As noted above, delivery, tissue attachment and retrieval features may be included in the LCP including those features shown in US PG Patent Publications 20150051610, and/or 20150025612, titled SYSTEM AND METHODS FOR CHRONIC FIXATION OF MEDICAL DEVICES, for example. Delivery, fixation and retrieval structures may also resemble that of the Micra™ (Medtronic) or Nanostim™ (St. Jude Medical) leadless pacemakers.

Figure 3:
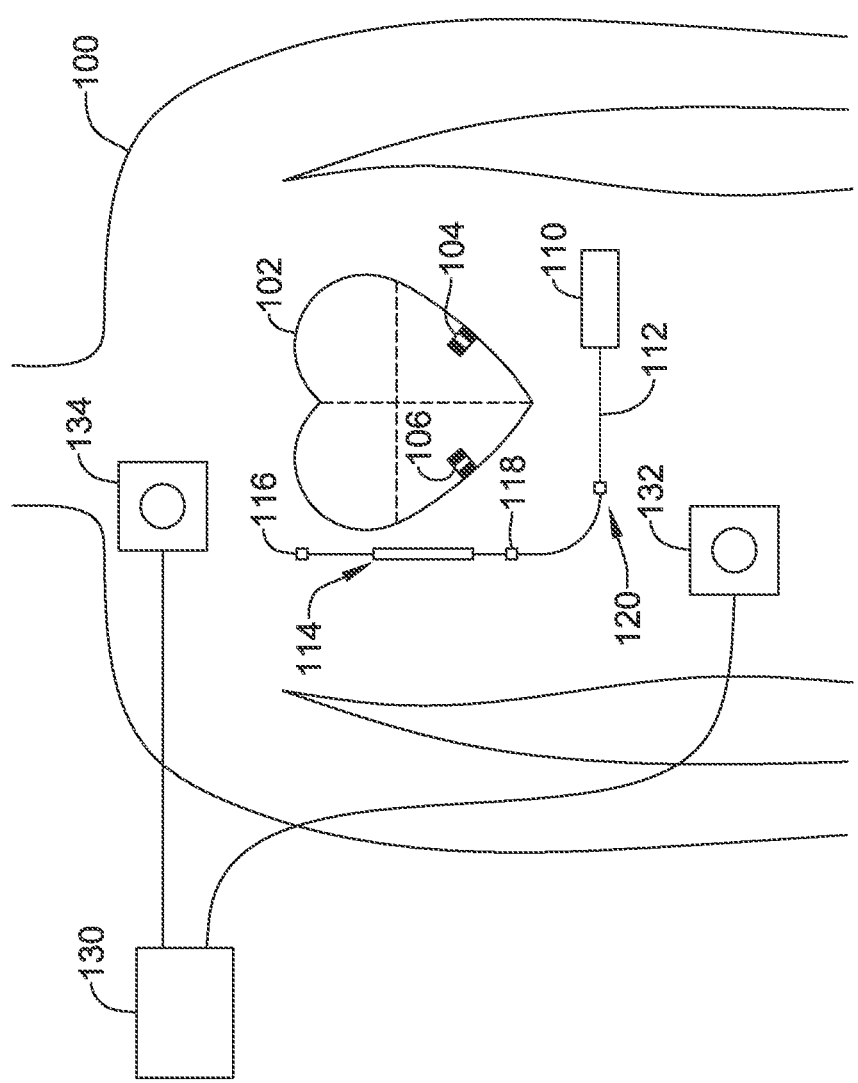
FIG. 3 shows a patient having a plurality of implantable medical devices.

FIG. 3 illustrates a patient 100 with an LCP 104 implanted inside the heart 102, in the left ventricle for illustrative purposes. Optionally a second LCP 106 is shown in the right ventricle of the heart 102. If desired further devices may be provided by having, for example, an LCP in one of the atria.

The patient 100 also has implanted another medical device in the form of a subcutaneous implantable defibrillator (SICD) having a left axillary canister 110 and a lead 112. The illustrative lead 112 is shown with a defibrillation coil 114 and sensing electrodes 116, 118 distal and proximal of the coil 114. A still more proximal sense electrode may also be provided as shown at 120. For securing the lead subcutaneously, one or more suture sleeves may be provided and/or the distal tip electrode 116 may be secured to the fascia by a suture or clip engaging a suture hole in the distal tip 116.

In some embodiments the lead may be as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE or, alternatively, the lead may have a bifurcation. Any suitable design for single, multiple, or bifurcated implantable leads may be used.

The lead 112 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANEOUS ELECTRODE INSERTION, and US PG Pat. Pub. No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference. A unitary implantation may involve the use of an elongated housing, such as shown in U.S. Pat. No. 6,647,292, titled UNITARY SUBCUTANEOUS ONLY IMPLANTABLE CARDIOVERTER-DEFIBRILLATOR AND OPTIONAL PACER, the disclosure of which is incorporated herein by reference.

A substernal placement may be used instead, with the distal end of the lead 112 (that is, the end distant from the canister 110) going beneath the sternum. Some examples of such placement are described in US PG Pat. Pub. No. 20170021159, titled SUBSTERNAL PLACEMENT OF A PACING OR DEFIBRILLATING ELECTRODE, the disclosure of which is incorporated herein by reference. Still another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference, in which the lead 112 may be inserted into an internal thoracic vein, for example, and placed in the internal thoracic vein at a desired location relative to the heart.

The devices 104, 106 (optionally), 110 may communicate with one another and/or with an external programmer 130 using conducted communication, in some examples. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver. Radiofrequency or inductive communication may be used instead. Alternatively the devices 104, 106 (optionally), 110 may communicate via inductive, optical, sonic, or radiofrequency communication, or any other suitable mode.

Subcutaneous implantable defibrillators may include, for example, the Emblem S-ICD System™ offered by Boston Scientific Corporation. Combinations of subcutaneous defibrillators and LCP devices are discussed, for example, in US PG Pat. Pub. Nos. 20160059025, 20160059024, 20160059022, 20160059007, 20160038742, 20160007873, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring).

A subcutaneous defibrillator and LCP may coordinate therapy such as by having the LCP deliver antitachycardia pacing in an attempt to convert certain arrhythmias before the subcutaneous defibrillator delivers a defibrillation shock. Two systems may coordinate to provide cardiac resynchronization therapy (CRT) as in U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, Ser. No. 15/684,264, titled CARDIAC RESYNCHRONIZATION USING FUSION PROMOTION FOR TIMING MANAGEMENT, Ser. No. 15/684,366, titled INTEGRATED MULTI-DEVICE CARDIAC RESYNCHRONIZATION THERAPY USING P-WAVE TO PACE TIMING, Ser. No. 15/710,118, titled MULTI-DEVICE CARDIAC RESYNCHRONIZATION THERAPY WITH MODE SWITCHING TIMING REFERENCE, and Ser. No. 15/793,475, titled MULTI-DEVICE CARDIAC RESYNCHRONIZATION THERAPY WITH TIMING ENHANCEMENTS, the disclosures of which are incorporated herein by reference.

In some examples, rather than one or more LCP devices as shown in FIG. 3, an SICD may be used in combination with a subcutaneous implantable monitor or a wearable monitoring apparatus (in either case, a "Monitor"). A Monitor may be, for example, a loop monitor that captures data under select conditions using two or more sensing electrodes on a housing thereof and/or attached thereto with a lead. Monitors have found use to assist in diagnosing cardiac conditions that may be infrequent or intermittent, or which have non-specific symptoms. In the context of the present invention, a Monitor, may be used to provide activity or posture information instead of an LCP, as described in any of the examples herein.

Several examples focus on using a left ventricular LCP 104. However, some examples may instead use a right ventricular LCP 106, and other examples may include both the left ventricular LCP 104 and right ventricular LCP 106. In other examples, a three implant system may include two LCP devices 104, 106, as well as a subcutaneous device such as the SICD 110 as shown. In still other examples, an atrial-placed LCP (not shown) may also be included or may take the place of one of the ventricular LCP devices 104, 106 and/or the SICD 110.

Figure 4:
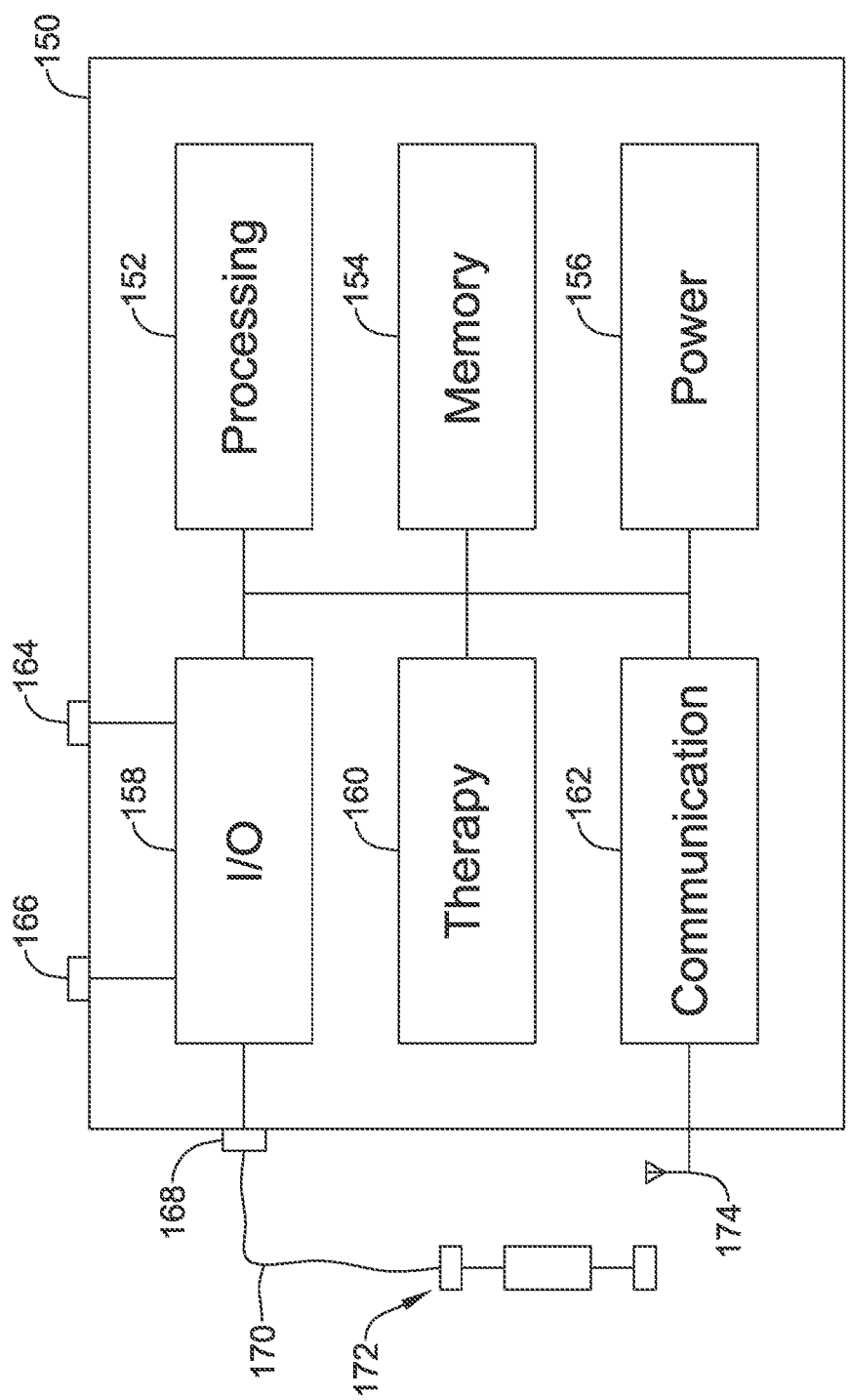
FIG. 4 shows an illustrative implantable medical device.

FIG. 4 illustrates a block diagram of an implantable medical device such as an SICD. The illustration indicates various functional blocks within a device 150, including a processing block 152, memory 154, power supply 156, input/output circuitry 158, therapy circuitry 160, and communication circuitry 162. These functional blocks make up at least some of the operational circuitry of the device. The I/O circuitry 158 can be coupled to one or more electrodes 164, 166 on the housing of the device 150, and may couple via a header 168 for attachment to one or more leads 170 having additional electrodes 172.

The processing block 152 will generally control operations in the device 150 and may include a microprocessor or microcontroller and/or other circuitry and logic suitable to its purpose. A state machine may be included. Processing block 152 may include dedicated circuits or logic for device functions such as converting analog signals to digital data, processing digital signals, detecting events in a biological signal, etc. The memory block may include RAM, ROM, flash and/or other memory circuits for storing device parameters, firmware or instruction code, and data related to the use, status, and history of the device 150. The power supply 156 typically includes one to several batteries, which may or may not be rechargeable depending on the device 150. For rechargeable systems there would additionally be charging circuitry for the battery (not shown) including for example a coil for receiving energy and regulating and rectification circuitry to provide received energy to a rechargeable battery or supercapacitor.

The I/O circuitry 158 may include various switches or multiplexors for selecting inputs and outputs for use. I/O circuitry 158 may also include filtering circuitry and amplifiers for pre-processing input signals. In some applications the I/O circuitry will include an H-Bridge to facilitate high power outputs, though other circuit designs may also be used. Therapy block 160 may include capacitors and charging circuits, modulators, and frequency generators for providing electrical outputs. A monitoring device may omit the therapy block 160 and may have a simplified I/O circuitry used simply to capture electrical or other signals such as chemical or motion signals.

The communication circuitry 162 may be coupled to an antenna 174 for radio communication (such as Medradio, ISM Band, Bluetooth, or other protocol or band), or alternatively to a coil for inductive communication, and/or may couple via the I/O circuitry 158 to a combination of electrodes 164, 166, 172, for conducted communication. Communication circuitry 162 may include a frequency generator, oscillator and mixer for creating output signals to transmit via the antenna 174. Some devices 150 may include a separate or even off-the shelf ASIC for the communications circuitry 162, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 4. For example, some devices 150 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 164, 166, but may omit the header 168 for coupling to lead 170, such as shown in U.S. Pat. No. 6,647,292, for example.

A device as in FIG. 4 may be embodied as a subcutaneous implantable defibrillator as shown above in FIG. 3. Alternatively a device 150 may be embodied as an implantable defibrillator and/or pacemaker as in US PG Pat. Pub. No. 20170021159, titled SUBSTERNAL PLACEMENT OF A PACING OR DEFIBRILLATING ELECTRODE, the disclosure of which is incorporated herein by reference. Still another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

Figure 5:
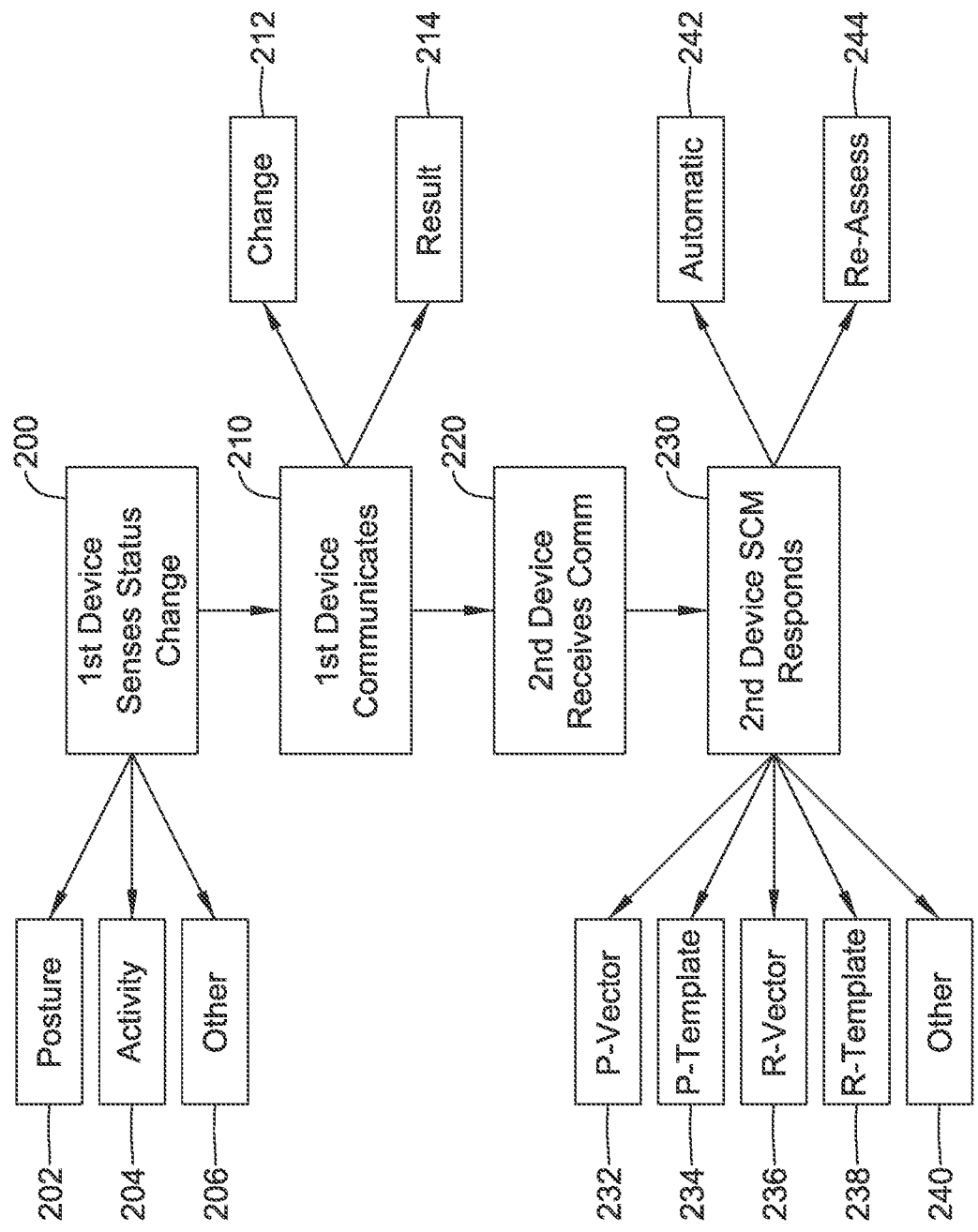
FIGS. 5-6 each show illustrative systems and methods of operation.
Figure 6:
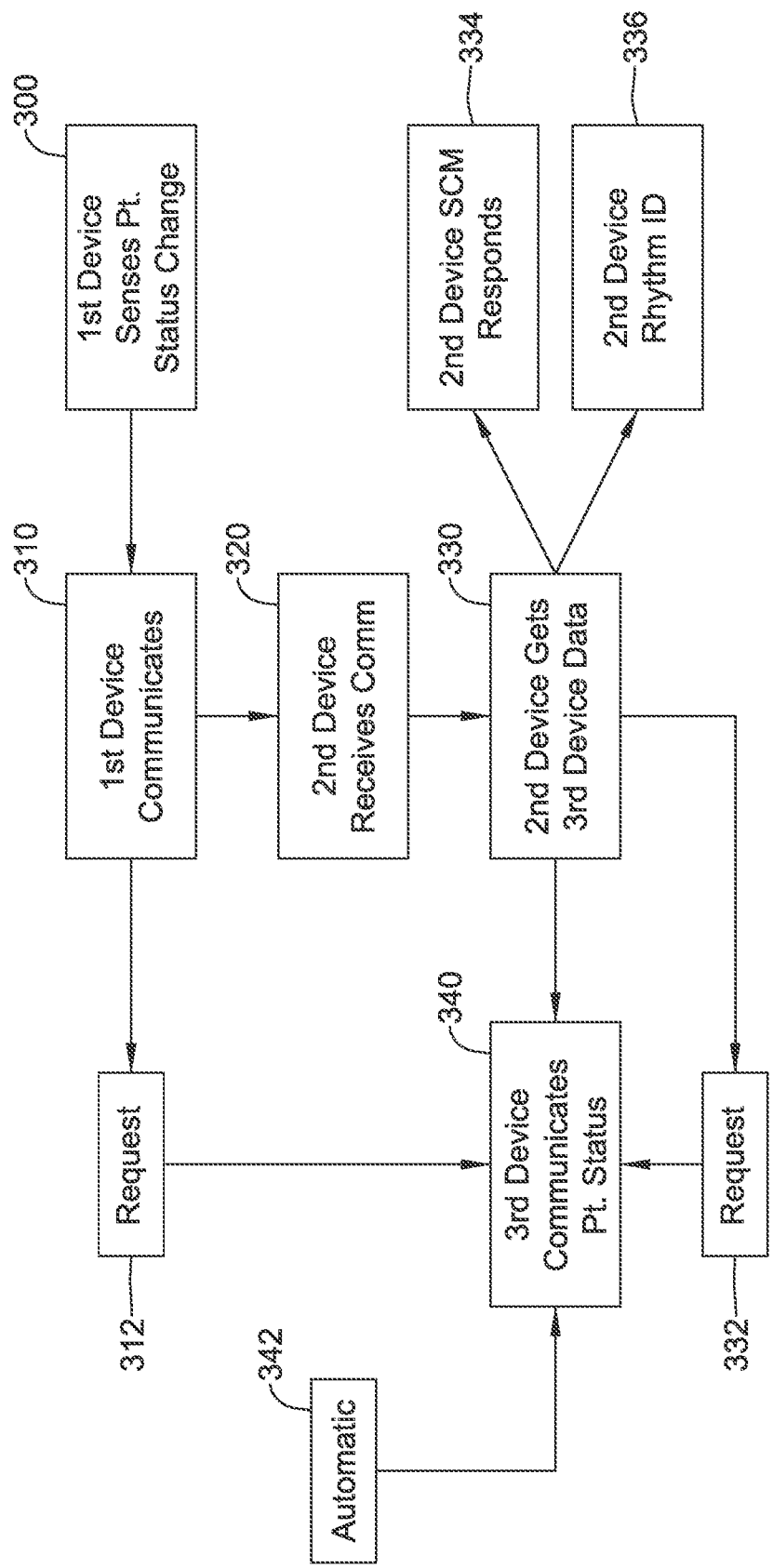

FIGS. 5-6 each show illustrative systems and methods of operation. In an example, a first device senses a patient status change, as indicated at 200. The first device then communicates, as indicated at 210, to a second implantable medical device, to indicate information about the patient status change. A second implantable medical device receives the communication at 220. In response to the received communication, the second implantable device responds with activation of a sensing configuration management (SCM) operation.

In a further illustration, the first device may sense the status change at block 200 using one or more inputs. The inputs for block 200 may include, for example, an input monitoring posture, as indicated at 202, using a posture monitoring function or functional block, such as an accelerometer and associated circuitry and processing instructions configured to identify a change in patient posture. The inputs for block 200 may instead, or in addition, include sensing for patient activity, as indicated at 204, using an activity monitoring function or functional block, such as by the use of an accelerometer and associated circuitry and processing instructions configured to identify a change in patient activity or activity level. Rather than an accelerometer, a temperature sensor has been proposed for monitoring patient activity 202, as for example may be done with an LCP located in a heart chamber and having a thermistor or other temperature responsive transducer. As is known in the art, measured temperature in the bloodstream can change in response to activity level changes. Other sensors may be used as indicated at block 206 to determine a change in patient status, such as by monitoring a cardiac electrical signal for changes in amplitude and/or rate of cardiac events.

The communication at block 210 may take place using any suitable mode of communication, such as conducted communication or telemetry using RF, optical, or acoustic communication. The content of the communication at block 210 may include a simple indication that a change has been observed, as indicated at 212, such as by indicating a change in posture (without necessarily identifying a beginning or ending posture), or a change in activity level with or without indication of whether activity level increased or decreased. The content of the communication at block 210 may instead, or in addition, indicate a result of the analysis by the first device, as indicated at 214 by, for example, indicating that the signature of the sensed posture 202 or activity 204 matches a template and/or one or more parameters corresponding to a posture (standing, seated, prone, lying on left or right side), and/or activity (exercise, walking, resting, sleeping).

The second device may receive at 220 a communicated signal and/or information using the same mode of communication as used to generate the signal at 210.

The second device can undertake a number of analyses in response to the received communication using a sensing configuration management function. For example, when acting in block 230, the second device may assess a selected vector for P-wave sensing 232, or a selected template for use in P-wave sensing at 234. In some examples, P-waves may be detected using the second device using a specifically selected vector for P-wave sensing using amplitude analysis in a defined window, or by comparing in a scrolling manner a portion of the cardiac signal to a P-wave template to observe a peak "match" between the received signal and the P-wave template. Some related concepts are further described in U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, which incorporated herein by reference. As discussed in the U.S. patent application Ser. No. 15/633,517, the P-wave detection by the second implantable device may be used to support CRT therapy in a variety of ways; other, non-CRT uses may be helpful as well, for example, to facilitate identification of atrial arrhythmia as the failure to find a P-wave may suggest atrial fibrillation. The P-wave vector analysis at 232 may include not only selecting a sensing vector, but also selecting filtering or other characteristics of the sensing approach such as setting a window for P-wave detection, if such a window is used.

For example, a P-wave vector selection routine may be run to identify which of several available sensing vectors are best suited for sensing in a given patient status, posture or activity by analyzing, for example, signal to noise ratio and/or amplitude or other characteristics for the P-wave. Examples of selecting of a sensing vector or combination of sensing vectors are discussed in, for example, U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 titled SENSING VECTOR SELECTION IN A CARDIAC STIMULUS DEVICE WITH POSTURAL ASSESSMENT, as well as in US PG Pat. Pub. Nos. 20170113053, titled SIGNAL QUALITY MONITORING FOR MULTIPLE SENSE VECTORS IN CARDIAC DEVICES, 20170113040, titled MULTI-VECTOR SENSING IN CARDIAC DEVICES WITH SIGNAL COMBINATIONS, 20170113050, titled MULTI-VECTOR SENSING IN CARDIAC DEVICES WITH DETECTION COMBINATIONS, and 20170112399, titled MULTI-VECTOR SENSING IN CARDIAC DEVICES USING A HYBRID APPROACH, the disclosures of which are incorporated herein by reference.

The P-wave vector analysis at 232 may include not only selecting a sensing vector, but also selecting filtering or other characteristics of the sensing approach such as setting a window for P-wave detection, if such a window is used. The P-wave template may be assessed by choosing a new template, or attempting to form a new template, such as by the application of methods disclosed in, for example, U.S. Pat. No. 7,477,935, titled METHOD AND APPARATUS FOR BEAT ALIGNMENT AND COMPARISON, and/or U.S. Pat. No. 7,376,458, titled METHOD FOR DEFINING SIGNAL TEMPLATES IN IMPLANTABLE CARDIAC DEVICES, the disclosures of which are incorporated herein by reference. Templates may take the form of a time ordered series of amplitude samples of a signal, as in the '935 and '458 patents, or may instead take the form of a dataset formed by analyzing a series of cardiac beat samples (P-waves for a P-wave template, or R-waves for an R-wave template, as desired) using a principle components analysis or a wavelet transform analysis. In some examples, templates may be formed using an average of several signals taken for several cardiac cycles. In other examples, templates may be formed by using data from a single cardiac cycle, and then confirmed by comparing results for several cardiac cycles to confirm that the template as formed would match several cardiac cycles worth of data. Other approaches may be used as desired.

In some examples, an R-wave vector 236 and/or R-wave template 238 may be analyzed and/or modified. For example, an R-wave vector selection routine may be run to identify which of several available sensing vectors are best suited for sensing in a given patient status, posture or activity by analyzing, for example, signal to noise ratio and/or amplitude or other characteristics for the R-wave. A number of vector selection examples for use in either R-wave or P-wave detection/analysis may be found in the above referenced patents and patent applications. The R-wave vector analysis at 232 may include not only selecting a sensing vector, but also selecting filtering or other characteristics of the sensing approach such as setting a window for R-wave detection, if such a window is used. Illustrative methods and/or devices described in US PG Pat. Pub. No. 20170156617, titled AUTOMATIC DETERMINATION OF SENSE CHANNEL FILTERING SCHEME, the disclosure of which is incorporated herein by reference, may be used as well for setting filtering characteristics for R-wave and/or P-wave detection channels.

In an illustrative example, a patient may be led through a series of postures following implant or fitting while a physician programmer is in operative communication with one or more implanted devices. As the patient holds a selected posture, the operator of the programmer indicates to the implanted (or wearable) system that the patient is in the selected posture, and template formation may take place, or vector selection may take place, or both, for P-wave detection and/or for R-wave detection. During such a process, the first medical device may monitor the output of the patient status sensor (such as an accelerometer configured for posture sensing) to determine a signature of the sensor output associated with the posture, while the second medical device performs analysis of the cardiac signals to selected templates and/or vectors for sensing. On completion of the data capture by the implanted devices, the physician programmer may indicate analysis is complete. The physician programmer may direct the method by requesting that the patient hold a series of postures in some order until a desired set of postures is reviewed, or the physician programmer may allow a user to select postures from a list. A set of postures may be checked such as upright/sitting, supine, right side, left side, prone, standing, etc. Programmer guided postural analysis is discussed as well in U.S. Pat. No. 8,483,843 titled SENSING VECTOR SELECTION IN A CARDIAC STIMULUS DEVICE WITH POSTURAL ASSESSMENT, the disclosure of which is incorporated herein by reference. Rather than a physician programmer, a patient remote control, home monitoring system, or even a patient mobile device running a medical application, may be used in such processes.

In another initialization example, a patient may be led through a series of activities or movements to capture one or more of posture and activity signals using the first medical device patient status sensor, while concomitantly capturing cardiac signal data with the second medical device. This would allow the first medical device to set parameters for identifying select postures, activities, and/or activity levels while allowing the second medical device to identify sensing characteristics, such as vectors, filtering, gain, and/or template selections that are useful while the patient is engaged in or adopts the tested postures and/or activities. Activities may include a patient's preferred mode of exercise (swimming, running, rowing, elliptical machine, etc.), selected daily activities (walking, sitting upright, simulated driving, climbing stairs, sleeping, resting, talking, etc.), or specially designed activities (Valsalva maneuver, for example).

Other steps may be taken as well, such as by using the communication at 220 to trigger a re-assessment of one or more recently detected cardiac cycles to ensure that the change in patient status (posture, activity or otherwise) has not affected signal detection accuracy. For example, a noise analysis or overdetection routine may be triggered. In an example, ordinary R-wave detection (such as in U.S. Pat. No. 8,565,878, titled ACCURATE CARDIAC EVENT DETECTION IN AN IMPLANTABLE CARDIAC STIMULUS DEVICE, the disclosure of which is incorporated herein by reference) may be augmented by activating a second rate analysis such as disclosed in US PG Patent Publications 20160045136, titled CALCULATION OF SELF-CORRELATION IN AN IMPLANTABLE CARDIAC DEVICE, 20160045132, titled PEAK SELECTION FOR SELF CORRELATION ANALYSIS OF CARDIAC RATE IN AN IMPLANTABLE MEDICAL DEVICES, and 20160045131, titled CARDIAC RATE TRACKING IN AN IMPLANTABLE MEDICAL DEVICE, the disclosures of which are incorporated herein by reference. Another example of a response is shown below in FIG. 6.

Modifications to one or more vector or template selections may take several forms. In some examples, automatic modification 242 may occur, as by having the second device SCM select a new vector 232, 236 and/or template 234, 238 in response to identification of an activity or posture by the first device if "results" 214 are communicated. Thus, for example, if the first device communicates that the patient has gone from laying down to standing, the second device may reconfigure its P-wave (if setup to sense P-waves) or R-wave analysis/vector/template to a default mode used for sensing while the patient is standing from a default mode for sensing while the patient is laying down. Thus block 242 may call for a switch of the vector or template.

In another example, the communication from the first device, whether it contains simply a change indication 212 or indicates a result 214, may trigger re-assessment or re-formation using vector selection and/or templating tools, rather than the second device blindly switching configurations. Re-assessment may include, for example, re-running vector selection or re-forming a template. Re-assessment may instead include, for example, confirming sensing vector quality or continued viability of a stored template by, for example, comparing to captured signals to determine whether high correlation exists. Thus block 244 may call for a modification or reformation of a template, or a re-assessment of vector selection.

In the above examples, vector selection may comprise selecting a single vector for use in cardiac signal sensing for R-wave or P-wave detection. In other examples, a plurality of vectors may be combined together for sensing purposes. For example, the raw signal, or filtered signal, may be combined in analog or digital form. Combinations may also be used later in the sensing process, for example, R-wave and/or P-wave detections may be made independently in plural vectors, with the results of such sensing combined together to identify incorrect detections such as over- or under-detections. The detections from multiple vectors may be combined together before or after independently correcting for noise and overdetection. Several examples of such combinations are discussed in US PG Pat. Pub. Nos. 20170113053, titled SIGNAL QUALITY MONITORING FOR MULTIPLE SENSE VECTORS IN CARDIAC DEVICES, 20170113040, titled MULTI-VECTOR SENSING IN CARDIAC DEVICES WITH SIGNAL COMBINATIONS, 20170113050, titled MULTI-VECTOR SENSING IN CARDIAC DEVICES WITH DETECTION COMBINATIONS, and 20170112399, titled MULTI-VECTOR SENSING IN CARDIAC DEVICES USING A HYBRID APPROACH, the disclosures of which are incorporated herein by reference.

In some examples, the second medical device may use the input from the first medical device to trigger a parallel analysis of both the previously used sensing configuration and a newly proposed sensing configuration prior to adopting the newly proposed sensing configuration. Thus, for example, when the first medical device communicates a patient status change, the second medical device may identify a proposed new sensing configuration and process incoming cardiac signal data using both the existing and proposed new sensing configuration to ensure accuracy/utility of the proposed new sensing configuration and safe handoff between the two configurations. To further facilitate handoff, the first medical device may communicate its analysis of cardiac rhythm, for example by indicating when detected cardiac cycles occur or a rate of such cardiac cycles, or other information, until the second medical device completes its changes or for a set period of time such as four to thirty seconds, or more or less.

FIG. 6 shows another example. In this example, the first medical device starts the process by sensing a patient status change, at 300, by, for example, sensing a change in patient activity level and/or posture. The first medical device then issues communication at 310, which a second medical device receives at 320. Next, the second medical device "gets" data from a third medical device, as indicated at 330, as explained below. The second device can then respond using a sensing configuration management tool, as indicated at 332 similar to that explained above relative to FIG. 5. In addition, the second medical device may perform rhythm identification, as indicated at 336, using data from one or both of the first medical device and/or third medical device, as explained below.

The third medical device incorporated at block 330 may communicate a patient status, as indicated at 340, to the second medical device. Such status may comprise, for example, detection of patient activity or activity level, posture, or other indications such as the level of local movement observed (for example, the third medical device may be in or on the heart to observe cardiac motion). Such communication at 340 may occur in several ways. In one example, the communication by the first medical device at 310 may incorporate or serve as a request to the third medical device to also communicate, as indicated at 312. Such a request 312 may be a separate communication from the first device to the third device, or the third device may be configured to listen for the communication by the first medical device to the second medical and respond thereto. Alternatively, the second medical device may request 332 that the third medical device provide a patient status by issuing a communication to the third medical device. Such a request 332 may be a specially addressed communication, or it may be that the third medical device is configured to listen for an acknowledgement by the second medical device of the first medical device communication and it responds thereto. In still another alternative, the third medical device may issue its communication at 340 automatically 342 such as by issuing a status update at intervals or when a patient status of a certain type (a change, or a status meeting defined criteria such as exceeding a level of activity/movement, a temperature above a threshold, or an electrical fault or cardiac rate condition, for example) is identified.

At block 336, the second medical device may compare data received from each of the first and third medical devices to determine whether a specific cardiac rhythm is taking place. In an example, one of the first and third medical devices is in or on a first chamber of the patient's heart, and the other of the first and third medical devices is in or on a second chamber of the patient's heart. During sinus rhythms, the action in one heart chamber generally correlates to action in another chamber on a cyclic basis; during arrhythmias, one or more chambers acts independently of other chambers. When the status indicated by the first and third medical devices correlate, this suggests sinus conditions such as sinus tachycardia (exercise induced, for example) or normal sinus rhythm, while if the statuses do not correlate, this suggests chamber originating arrhythmia such as atrial flutter, atrial fibrillation (AF) (more particularly, AF which does not conduct to the ventricles), ventricular tachyarrhythmia, and/or ventricular fibrillation. Further, if it is known which chamber each of the first and third medical devices is in, then this may aid further in rhythm identification at block 336. The table suggests some combinations:

| $1^{st}$ and $3^{rd}$ Correlated? | $1^{st}$ Device Location | $3^{rd}$ Device Location | $1^{st}$ Device Motion | $3^{rd}$ Device Motion | Likely Rhythm |
|---|---|---|---|---|---|
| Yes | Ventricular | Atrial | Fast, Regular | Fast, Regular | Sinus Tachycardia |
| No | Ventricular | Atrial | Fast, Irregular | Slow, Irregular | Ventricular Fibrillation |
| No | Ventricular | Atrial | Fast, Regular | Slow, Irregular | Ventricular Tachyarrhythmia |
| No | Ventricular | Atrial | Slow, Irregular | Fast, Irregular | Sporadically Conducted Atrial Fibrillation |
| No | Ventricular | Atrial | Slow, Regular | Fast, Irregular | Non-Conducted Atrial Fibrillation |

In some examples, a ventricular originating tachyarrhythmia with retrograde conduction may be observed by the use of timing between when an atrial device and a ventricular device begins observing a high rate condition through motion or electrical detection, as in such cases the ventricular device may be the first to detect the high rate condition with the atrial device not picking up the high rate until after retrograde conduction sets in.

In some examples, a rhythm identification at 336 may be used as one factor among several to delay or accelerate therapy, or make a determination as to which of several available therapies may be applied; for example, if block 336 finds likely ventricular tachyarrhythmia, this may be a factor causing a system to deliver an anti-tachycardia pacing therapy rather than a defibrillation therapy. A rhythm identification at 336 may be treated as conclusive in some other examples. Thus, for example, if a rhythm is identified as atrial fibrillation, therapy may be withheld for a period of time, or parameters to sensing may be applied to inhibit therapy or require extra evidence of ventricular arrhythmia before therapy delivery.

A number of non-limiting illustrative embodiments follow, some of which use means language which is reiterated here to provide references to examples associated with the means language to aspects of the above description. Such references should be understood as exemplary and illuminating, rather than limiting, and such means language should be interpreted in light of the entire description and drawings.

A first non-limiting illustrative embodiment takes the form of a system for treating a patient comprising: a first medical device comprising a status sensor for at least sensing changes in patient status (such a status sensor may be an electrical sensor or a mechanical sensor in respective modules 56, 58 of FIG. 2 and may determine posture 202, activity 204, or other conditions 206, as indicated by FIG. 5 and further described above), and first communication means (such first communication means may take the form of a communications module 52 as shown in FIG. 2 and described above); and a second medical device taking the form of an implantable medical device comprising a plurality of electrodes for receiving cardiac electrical signals, sensing means for sensing cardiac rhythms of the patient using at least the received cardiac electrical signals (such sensing means may take the form of dedicated circuits in an I/O block 158 for one or more of selecting, filtering and/or converting analog signals to digital form, as well as stored instruction sets in memory 154 for operation by processing block 152 and/or dedicated circuits such an application specific integrated circuit or a logic and processing block in the processing block 152 and/or I/O 158 of FIG. 4), and a second communication means (such as noted at block 162 in FIG. 4 and described above); wherein the first communication means is configured to communicate to the second communication means, and the second communication means is configured to at least receive communication from the first communication means; further wherein: the first medical device comprises status assessment means for determining that the patient status is changing or has changed, the status assessment means further configured to use the first communication means to communicate to the second medical device in response to determining that the patient status is changing or has changed (such an assessment means may be implemented in the processing module 60 in FIG. 2 using, if desired, dedicated circuitry for amplification, filtering, conversion and thresholding circuits, or using a processor or state machine with reference to operable instructions stored in a memory); and the second medical device comprises sensing configuration management (SCM) means configured to analyze or adjust a sensing configuration used by the sensing means in response to the second communication means receiving a communication from the first communication means (such a sensing configuration management means may include operable instructions stored in memory 154 for execution by processing block 152 in FIG. 4, and/or dedicated circuitry in device 150 of FIG. 4, to implement block 230 of FIG. 5 using, for example, P-wave sensing vector analysis 232, P-wave template analysis 234, R-wave sensing vector analysis 236, R-wave template analysis 238, and/or other analyses 240 as describe further above in relation to FIG. 5).

Additionally or alternatively to the first non-limiting illustrative embodiment, the status sensor may include a posture sensor for at least sensing changes in patient posture; and the status assessment means may include a posture assessment means for determining that the patient posture is changing or has changed.

Additionally or alternatively to the first non-limiting illustrative embodiment and variants thereof, the status sensor may include an activity sensor for at least sensing changes in patient activity level; and the status assessment means may include an activity assessment means for determining the patient activity level is changing or has changed.

Additionally or alternatively to the first non-limiting illustrative embodiment and variants thereof, the SCM means may be configured to select from at least first and second sensing vectors for the sensing means of the second medical device to use in sensing atrial cardiac activity of the patient.

Additionally or alternatively to the first non-limiting illustrative embodiment and variants thereof, the SCM means may be configured to select from at least first and second sensing vectors for the sensing means of the second medical device to use in sensing ventricular cardiac activity of the patient.

Additionally or alternatively to the first non-limiting illustrative embodiment and variants thereof, the SCM may be configured to analyze cardiac signal data prior to select a sensing vector in response to receiving a communication from the first medical device.

Additionally or alternatively to the first non-limiting illustrative embodiment and variants thereof, the SCM may be configured to automatically select a sensing vector in response to receiving a communication from the first medical device by using a current patient status to determine which of a plurality of available sensing vectors to use.

Additionally or alternatively to the first non-limiting illustrative embodiment and variants thereof, the SCM means may be configured to select from at least first and second templates of cardiac ventricular events.

Additionally or alternatively to the first non-limiting illustrative embodiment and variants thereof, the SCM means may be configured to select from at least first and second templates of cardiac atrial events.

Additionally or alternatively to the first non-limiting illustrative embodiment and variants thereof, the SCM may be configured to analyze cardiac signal data prior to select a template in response to receiving a communication from the first medical device.

Additionally or alternatively to the first non-limiting illustrative embodiment and variants thereof, the SCM may be configured to automatically select a template in response to receiving a communication from the first medical device by using a current patient status to determine which of a plurality of available templates to use.

Additionally or alternatively to the first non-limiting illustrative embodiment and variants thereof, the first medical device may be a leadless cardiac pacemaker configured to be placed in or on the heart and which lacks any leads, and the second device may be an implantable defibrillator (such a system is shown, for example, in FIG. 3)

Additionally or alternatively to the first non-limiting illustrative embodiment and variants thereof, the system further comprises a third medical device comprising a status sensor for sensing at least one of a patient status or changes in patient status, and third communication means configured for communication with at least the second medical device; wherein the second medical device may be configured to observe data received from each of the first and third medical devices as to the patient status and determine, or augment a determination of, the patient's cardiac rhythm (a system with each of first, second and third devices is again shown in FIG. 3). In a further extension of this addition or alternative, each of the first and third medical devices may be a leadless cardiac pacemaker for implantation on or adjacent the heart; the second medical device may be an implantable defibrillator; the status sensors of the first and third medical devices may comprise motion sensors; and the second medical device may be configured to differentiate at least one of atrial fibrillation, ventricular tachycardia, and ventricular fibrillation, from sinus rhythm using the data received from each of the first and third medical devices as to the patient status.

Additionally or alternatively to the first non-limiting illustrative embodiment and variants thereof, the sensing means of the second medical device may be configured for sensing P-waves and R-waves of the patient's heart in separate data streams with: a P-wave detection sensing vector and P-wave template used in a data stream for the P-waves; and an R-wave detection sensing vector and R-wave template used in a data stream for the R-waves; and further wherein, in response to receiving a communication from the first medical device in response to a sensed change in patient status, the SCM means may be configured to analyze and/or change at least two of these settings: the P-wave detection sensing vector; the P-wave template; the R-wave detection sensing vector; and the R-wave template (FIG. 5 illustrates such details at blocks 232, 234, 236, 238, relative to block 230).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for treating a patient comprising:
   a first medical device comprising a status sensor for at least sensing changes in patient status, and a first communication circuit for generating a communication output;
   a second medical device in the form of an implantable medical device comprising a plurality of electrodes for receiving cardiac electrical signals, operational circuitry operable to sense cardiac rhythms of the patient using at least the received cardiac electrical signals, and a second communication circuit;
   wherein the first communication circuit is configured to communicate to the second communication circuit, and the second communication circuit is configured to at least receive communication from the first communication circuit; further wherein:
   the first medical device is configured to use the first communication circuit to communicate to the second communication circuit in response to sensing via the status sensor that the patient status is changing or has changed; and
   the second medical device operational circuitry is configured to analyze or adjust a sensing configuration used by the second medical device to sense cardiac rhythms of the patient in response to the second communication circuit receiving a communication from the first communication circuit.

2. The system of claim 1 wherein:
   the status sensor includes a posture sensor for at least sensing changes in patient posture;
   the first medical device is configured to use the first communication circuit to communicate to the second communication circuit in response to the posture sensor sensing that the patient posture is changing or has changed; and the second medical device is configured to analyze a sensing vector configuration used for cardiac activity sensing in response to the first medical device communicating in response to a change in posture status of the patient.

3. The system of claim 1 wherein:

the status sensor includes an activity sensor for at least sensing changes in patient activity level; and the first medical device is configured to use the first communication circuit to communicate to the second communication circuit in response to the activity sensor sensing that the patient activity level is changing or has changed; and the second medical device is configured to analyze a sensing vector configuration used for cardiac activity sensing in response to the first medical device communicating in response to a change in activity status of the patient.

4. The system of claim 1 wherein:

the status sensor includes a posture sensor for at least sensing changes in patient posture;

the first medical device is configured to use the first communication circuit to communicate to the second communication circuit in response to the posture sensor sensing that the patient posture is changing or has changed; and the second medical device is configured to modify, reform, or switch a template used in analyzing cardiac activity in response to the first medical device communicating in response to a change in posture status of the patient.

5. The system of claim 1 wherein:

the status sensor includes an activity sensor for at least sensing changes in patient activity level; and the first medical device is configured to use the first communication circuit to communicate to the second communication circuit in response to the activity sensor sensing that the patient activity level is changing or has changed;

the second medical device is configured to modify, reform, or switch a template used in analyzing cardiac activity in response to the first medical device communicating in response to a change in activity status of the patient.

6. The system as in claim 1 further comprising a third medical device comprising a status sensor for sensing at least one of a patient status or changes in patient status, and third communication circuit configured for communication to at least the second communication circuit;

wherein the operational circuitry of the second medical device is configured to observe data received from each of the first and third medical devices as to the patient status and determine, or augment a determination of, the patient's cardiac rhythm.

7. The system as in claim 6 wherein:

each of the first and third medical devices is a leadless cardiac pacemaker for implantation on or adjacent the heart;

the second medical device is an implantable defibrillator;

the status sensors of the first and third medical devices comprise motion sensors; and the second medical device is configured to differentiate at least one of atrial fibrillation, ventricular tachycardia, and ventricular fibrillation, from sinus rhythm using the data received from each of the first and third medical devices as to the patient status.

8. A system as in claim 1 wherein:

the operational circuitry of the second medical device is configured for sensing P-waves and R-waves of the patient's heart in separate data streams with:

a P-wave detection sensing vector and P-wave template used in a data stream for the P-waves; and an R-wave detection sensing vector and R-wave template used in a data stream for the R-waves; and further wherein the operational circuitry is configured to analyze and/or change at least two of these settings in response to receiving a communication generated by the first medical device in response to a sensed change in patient status:

the P-wave detection sensing vector;

the P-wave template;

the R-wave detection sensing vector; and the R-wave template.

9. A system as in claim 1 wherein the first medical device is a leadless cardiac pacemaker configured for implantation in or on the heart of a patient, and the second medical device is an implantable defibrillator.

10. A system as in claim 1 wherein the first and second communications circuits are configured to use conducted communication in which a communications output is generated using electrodes that contact patient tissue, and a communication input is taken using electrodes that contact patient tissue.

11. A system as in claim 1 wherein the first and second communications circuits are configured to use antennae to communicate with one another.

12. An implantable medical device (IMD) comprising a housing containing operational circuitry, a lead having one or more electrodes thereon and coupled to the operational circuitry such that the operational circuitry can use the one or more electrodes to sense cardiac rhythms of a patient, the operational circuitry including a communication circuit for communicating with a second medical device, wherein the operational circuitry is configured to:

receive a communication using the communication circuit from the second medical device, the communication indicating a change in a patient status; and in response to receiving the communication indicating a change in patient status, analyze or adjust a sensing configuration used by the operational circuitry to sense cardiac rhythms of the patient.

13. The IMD of claim 12 wherein:

the communicated patient status is a patient posture or a change in patient posture; and the IMD is configured to analyze a sensing vector configuration used for cardiac activity sensing in response to the second medical device communicating a patient posture or a change in patient posture.

14. The IMD of claim 12 wherein:

the communicated patient status is a patient activity level; and the IMD is configured to analyze a sensing vector configuration used for cardiac activity sensing in response to the second medical device communicating a change in patient activity level.

15. The IMD of claim 12 wherein:

the communicated patient status is a patient posture or a change in patient posture; and the IMD is configured to modify, reform, or switch a template used for cardiac activity sensing in response to the second medical device communicating a change in patient posture.

16. The IMD of claim 12 wherein:
the communicated patient status is a patient activity level; and
the IMD is configured to modify, reform, or switch a template used for cardiac activity sensing in response to the second medical device communicating a change in activity level of the patient.

17. The IMD of claim 12 wherein the communication circuitry is configured to communicate with a third medical device and receive patient status information therefrom;
wherein the operational circuitry of the IMD is configured to observe data received from each of the second and third medical devices as to the patient status and determine, or augment a determination of, the patient's cardiac rhythm.

18. The IMD of claim 17 wherein:
the operational circuitry is configured to receive patient status information from the second and third medical devices comprising motion information generated by motion sensors of the second and third medical devices; and
the IMD is configured to differentiate at least one of atrial fibrillation, ventricular tachycardia, and ventricular fibrillation, from sinus rhythm using the motion data received from each of the second and third devices.

19. The IMD of claim 12 wherein:
the operational circuitry of the IMD is configured for sensing P-waves and R-waves of the patient's heart in separate data streams with:
a P-wave detection sensing vector and P-wave template used in a data stream for the P-waves; and
an R-wave detection sensing vector and R-wave template used in a data stream for the R-waves; and
in response to receiving a communication indicating a change in patient status from the second medical device, the operational circuitry of the IMD is configured to analyze and/or change at least two of these settings:
the P-wave detection sensing vector;
the P-wave template;
the R-wave detection sensing vector; and
the R-wave template.

20. A method of operation in an implantable medical device system, the system comprising:
a first medical device comprising a status sensor for at least sensing changes in patient status, and a first communication circuit for generating a communication output;
a second medical device in the form of an implantable medical device comprising a plurality of electrodes for receiving cardiac electrical signals, operational circuitry operable to sense cardiac rhythms of the patient using at least the received cardiac electrical signals, and a second communication circuit configured to receive communication from the first medical device;
the method comprising:
the first medical device sensing a change in patient status;
the first medical device communicating to the second medical device to in response to a change in patient status;
the second medical device receiving the communication from the first medical device in response to a change in patient status and, in response thereto, the second medical device analyzing or adjusting a sensing configuration used by the second medical device to sense cardiac rhythms of the patient.

* * * * *